United States Patent
Gonopolskiy et al.

(10) Patent No.: US 8,718,736 B2
(45) Date of Patent: May 6, 2014

(54) PHYSIOLOGICAL SENSOR WITH OFFSET ADHESIVE LAYER

(75) Inventors: Oleg Gonopolskiy, West Bloomfield, MI (US); Arik Anderson, Birmingham, MI (US); Melissa Muto, Royal Oak, MI (US); Matthew Stimpson, Macomb, MI (US); Richard Morabito, Grosse Ile, MI (US)

(73) Assignee: Covidien LP, Mansfield, MA (US)

( * ) Notice: Subject to any disclaimer, the term of this patent is extended or adjusted under 35 U.S.C. 154(b) by 738 days.

(21) Appl. No.: 12/842,809

(22) Filed: Jul. 23, 2010

(65) Prior Publication Data

US 2011/0021901 A1    Jan. 27, 2011

Related U.S. Application Data

(60) Provisional application No. 61/228,090, filed on Jul. 23, 2009.

(51) Int. Cl.
*A61B 5/00* (2006.01)

(52) U.S. Cl.
USPC .................................................... 600/323

(58) Field of Classification Search
USPC .................................................... 600/323
See application file for complete search history.

(56) References Cited

U.S. PATENT DOCUMENTS

| | | | | |
|---|---|---|---|---|
| 4,121,573 A * | 10/1978 | Crovella et al. | | 600/382 |
| 4,825,879 A * | 5/1989 | Tan et al. | | 600/344 |
| 4,911,169 A * | 3/1990 | Ferrari | | 600/384 |
| 5,090,410 A * | 2/1992 | Saper et al. | | 602/41 |
| 5,209,230 A * | 5/1993 | Swedlow et al. | | 600/322 |
| 5,226,417 A * | 7/1993 | Swedlow et al. | | 600/336 |
| 5,465,714 A * | 11/1995 | Scheuing | | 600/323 |
| RE36,000 E * | 12/1998 | Swedlow et al. | | 600/454 |
| 6,198,951 B1 * | 3/2001 | Kosuda et al. | | 600/323 |
| 6,256,523 B1 * | 7/2001 | Diab et al. | | 600/323 |
| 7,160,251 B2 * | 1/2007 | Neel et al. | | 600/365 |
| 7,190,987 B2 * | 3/2007 | Lindekugel et al. | | 600/344 |
| 7,418,284 B2 * | 8/2008 | DeLonzor et al. | | 600/310 |
| 7,680,522 B2 * | 3/2010 | Andersohn et al. | | 600/310 |
| 7,869,849 B2 * | 1/2011 | Ollerdessen et al. | | 600/323 |
| 7,869,855 B2 * | 1/2011 | Meyer et al. | | 600/391 |
| 7,899,510 B2 * | 3/2011 | Hoarau | | 600/344 |
| 2002/0004640 A1 * | 1/2002 | Conn et al. | | 604/20 |
| 2002/0038082 A1 * | 3/2002 | Chin | | 600/323 |
| 2004/0143172 A1 * | 7/2004 | Fudge et al. | | 600/344 |
| 2005/0197550 A1 * | 9/2005 | Al-Ali et al. | | 600/323 |
| 2006/0084852 A1 * | 4/2006 | Mason et al. | | 600/344 |
| 2006/0089585 A1 * | 4/2006 | Takemura et al. | | 602/58 |
| 2006/0135884 A1 * | 6/2006 | Hack et al. | | 600/547 |
| 2006/0276700 A1 * | 12/2006 | O'Neil et al. | | 600/344 |
| 2007/0073121 A1 * | 3/2007 | Hoarau et al. | | 600/323 |

(Continued)

*Primary Examiner* — Rodney Fuller
(74) *Attorney, Agent, or Firm* — Harness, Dickey & Pierce, PLC

(57) ABSTRACT

An exemplary sensor includes a sensor pad defining a perimeter, a light source, a light detector, and an adhesive layer. The light source is configured to generate near-infrared light and transmit the near-infrared light through part of a patient's body. The light detector is configured to receive the near-infrared light generated by the light source after it has traveled through part of the patient's body. The light received by the light detector indicates an amount of oxygen in the part of the patient's body through which the near-infrared light traveled. The adhesive layer is offset relative to the sensor pad to, for example, allow a clinician to easily remove the sensor from the patient.

21 Claims, 3 Drawing Sheets

(56) References Cited

U.S. PATENT DOCUMENTS

| | | |
|---|---|---|
| 2008/0242958 A1* | 10/2008 | Al-Ali et al. .................. 600/323 |
| 2008/0275327 A1* | 11/2008 | Faarbaek et al. ............. 600/382 |
| 2009/0131770 A1* | 5/2009 | Scheuing et al. ............. 600/310 |
| 2009/0131774 A1* | 5/2009 | Sweitzer et al. ............. 600/323 |
| 2010/0100077 A1* | 4/2010 | Rush et al. .................. 604/890.1 |
| 2012/0035443 A1* | 2/2012 | Hoarau et al. ................ 600/324 |

* cited by examiner

PHYSIOLOGICAL SENSOR WITH OFFSET ADHESIVE LAYER

CROSS-REFERENCE TO RELATED APPLICATIONS

This application claims priority to U.S. Ser. No. 61/228,090 filed Jul. 23, 2009, which is incorporated herein by reference in its entirety.

BACKGROUND

Near-infrared sensors are used in the medical industry to measure the amount of oxygen saturation in a patient's blood or tissue. The sensor includes an adhesive so that the sensor will stay in place relative to the patient's body. The adhesive extends beyond the perimeter of the sensor to allow the sensor to fit the contours of the patient's body and to increase the holding ability of the sensor. However, this makes the sensor difficult to remove. In particular, it is difficult for clinicians to peel the adhesive part of the sensor from the patient's skin, leaving clinicians with few options. One option is to pull on the cable connecting the sensor to a controller or display device. Doing so, however, creates a negative pressure under the sensor. This negative pressure can injure the patient's skin and tissue, especially when the sensor is used with neonates. Accordingly, a sensor is needed that provides the clinician with an option to remove the sensor without creating the damaging negative pressure.

DETAILED DESCRIPTION

An exemplary physiological sensor that allows the clinician to remove the sensor without significant risk of damaging the patient's skin or tissue includes a sensor pad defining a perimeter, a light source, a light detector, and an adhesive layer. The adhesive layer is offset relative to the sensor pad. For example, one part of the adhesive layer may extend beyond the perimeter of the sensor pad and another part of the adhesive layer may be substantially flush with the perimeter of the sensor pad. Alternatively, part of the adhesive layer may extend beyond the perimeter of the sensor pad while part of the sensor pad extends beyond an edge of the adhesive layer.

When placed on a patient, the light source generates near-infrared light and transmits the near-infrared light through part of the patient's body. The light detector receives the near-infrared light generated by the light source after the light has traveled through part of the patient's body. The near-infrared light received by the light detector indicates an amount of oxygen in the part of the patient's body through which the light traveled. Thus, the sensor may be used to detect oxygen saturation. The offset adhesive layer allows the clinician to remove the sensor without creating the negative pressure that may damage the patient's skin or other tissue. To discourage the clinician from pulling on the cable to remove the sensor from the patient, the adhesive layer is offset such that the portion of the sensor pad that is either flush or extending beyond the adhesive layer is spaced from the cable.

Figure 1:
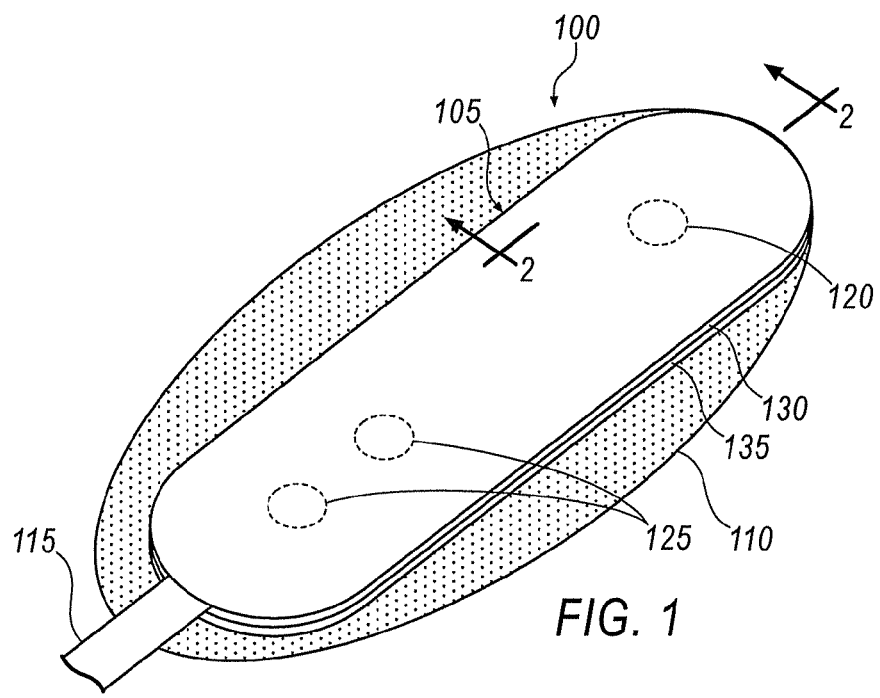
FIG. 1 illustrates an exemplary sensor having an adhesive layer offset from a sensor pad.

FIG. 1 illustrates an exemplary sensor 100 that allows a clinician to remove the sensor without creating a negative pressure that could damage the patient's skin and tissue. The sensor 100 may take many different forms and include multiple and/or alternate components and facilities. While an exemplary sensor 100 is shown, the exemplary components illustrated in the figures are not intended to be limiting. Indeed, additional or alternative components and/or implementations may be used.

As illustrated in FIG. 1, the sensor 100 includes a sensor pad 105, an adhesive layer no, and a cable 115. The sensor pad 105 may include any device configured to house a light source 120 and a light detector 125. The sensor pad 105 may be at least partially formed from a flexible material so that the sensor pad 105 may bend to fit the contours of the patient's body. The sensor pad 105 may be formed from one or more layers. For instance, the sensor pad 105 may include a top layer 130 that is spaced from the patient's skin when the sensor 100 is placed on the patient. The top layer 130 may include a light blocking material. That is, the top layer 130 may be opaque to near-infrared and other types of light, such as ambient light. The bottom layer 135 may be between the top layer 130 and the patient's skin when the sensor 100 is placed on the patient. The bottom layer 135 may define one or more openings (not shown) to allow the near-infrared light generated by the light source 120 to travel into the patient's body and to allow the light detectors 125 to receive the light after it has traveled through part of the patient's body. Both the top and bottom layers 130 and 135 may be formed from the flexible material. In addition, the sensor pad 105 may define a perimeter. In one exemplary implementation, the top layer 130, the bottom layer 135, or both, may define the perimeter, that is, the outer edge, of the sensor pad 105.

The adhesive layer no is the layer closest to the patient's skin when the sensor 100 is disposed on the patient. As such, the adhesive layer no may include any material that allows the sensor pad 105 to adhere to the patient's skin. For instance, the adhesive layer no may include a pressure sensitive adhesive and/or an adhesive having hydrocolloid properties. The pressure sensitive adhesive may include any adhesive that creates a bond when the adhesive layer no is pressed against the patient's skin. For instance, the clinician may place the sensor 100 on the patient so that the adhesive layer no is in contact with the patient's skin. The clinician may apply a pressure to the top of the sensor pad 105 and to the edges of the adhesive layer no, causing the adhesive to adhere the sensor pad 105 to the patient. The hydrocolloid adhesive may include any adhesive with a tackiness that increases as the temperature of the adhesive increases. For instance, as the patient's skin temperature increases, the hydrocolloid adhesive provides a stronger bond to the patient's skin. The adhesive layer 110 is disposed on the bottom layer 135 of the sensor pad 105.

The adhesive layer no is offset relative to the sensor pad 105. That is, the adhesive layer no may have one part that extends beyond the perimeter of the sensor pad 105 while another part of the adhesive layer no is substantially flush with the perimeter of the sensor pad 105 at a location spaced from the cable 115 to allow the clinician to easily remove the sensor 100 without creating a negative pressure on the patient's skin. For example, the part of the sensor pad 105 that is flush with the adhesive layer no gives the clinician something to pull other than the cable 115 when removing the sensor 100 from the patient's skin. Alternatively, one part of the adhesive layer no may extend beyond the perimeter of the sensor pad 105 while part of the sensor pad 105 extends beyond an edge of the adhesive layer no. This alternative implementation is discussed in greater detail below with respect to FIGS. 3 and 6.

The cable 115 may include any device that allows a controller (not shown) to communicate with and/or control the light source 120 and the light detector 125. For instance, the light source 120 and light detector 125 may be disposed on a flexible printed circuit board (not shown) with traces that carry control signals from the controller. The control signals may be transmitted from the controller to the traces of the flexible printed circuit board via wires that are disposed within the cable 115. The cable 115 may further include signals generated by the light detector 125 that indicate the oxygen saturation of patient blood and/or tissue.

As illustrated in FIG. 1, the cable 115 may generally extend in the same direction as the sensor pad 105. Further, the part of the sensor pad 105 that is flush with the edge of the adhesive portion may be opposite the part of the sensor pad 105 from which the cable 115 extends to discourage the clinician from pulling on the cable 115 to remove the sensor 100 from the patient's body.

The light source 120 may include any device that is able to generate near-infrared light and transmit the near-infrared light into the patient's body in response to a control signal received from the controller. For example, the light source 120 may include a light emitting diode (LED) or a laser diode. The light source 120 may be disposed on a flexible printed circuit board (not shown) disposed on the top layer 130, the bottom layer 135, or both. The light source 120 may be aligned with an opening (not shown) in the bottom layer 135 so that the light generated by the light source 120 may travel into the patient's body. The sensor too may include any number of light sources 120. As illustrated in FIG. 1, the sensor 100 includes one light source 120.

The light detector 125 may include any device that is able to receive the light generated by the light source 120 and generate a signal representative of the light received. For example, the light detector 125 may include a photodiode. The light detector 125 may be disposed on a flexible printed circuit board (not shown) disposed on the top layer 130, the bottom layer 135, or both. The light detector 125 may be aligned with one or more openings (not shown) in the bottom layer 135 so that the light detector 125 may receive the light generated by the light source 120. The sensor 100 may include any number of light detectors 125. For instance, as illustrated in FIG. 1, the sensor 100 includes two light detectors 125.

Figure 2:
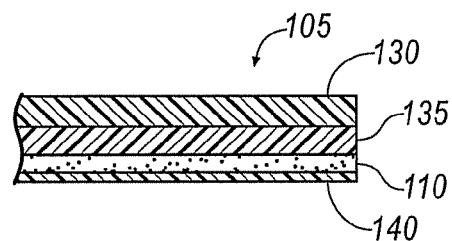
FIG. 2 illustrates an exemplary cross-section of the sensor of FIG. 1 taken along the line 2-2.

FIG. 2 illustrates an exemplary cross-sectional view of the sensor 100 of FIG. 1 taken along the line 2-2. As illustrated, the sensor 100 includes the top layer 130 and the adhesive layer 110 disposed on the bottom layer 135. Further, a liner 140 is disposed on the adhesive layer 110 to protect the adhesive prior to placing the sensor 100 on the patient. For example, the liner 140 prevents the adhesive layer 110 from sticking to unintended objects. The liner 140 may be removed before it is placed on the patient.

As illustrated in FIG. 2, the top layer 130, the bottom layer 135, the adhesive layer 110, and the liner 140 are substantially flush with one another on one side of the sensor 100, while the adhesive layer 110 and the liner 140 extend beyond the perimeter defined by the top and bottom layers 130 and 135 on an opposite side of the sensor 100. To remove the sensor 100 without a significant risk of causing damage to the patient's skin, the clinician may peel the sensor 100 from the side of the sensor 100 where the top layer 130, the bottom layer 135, and the adhesive layer 110 are substantially flush.

Figure 3:
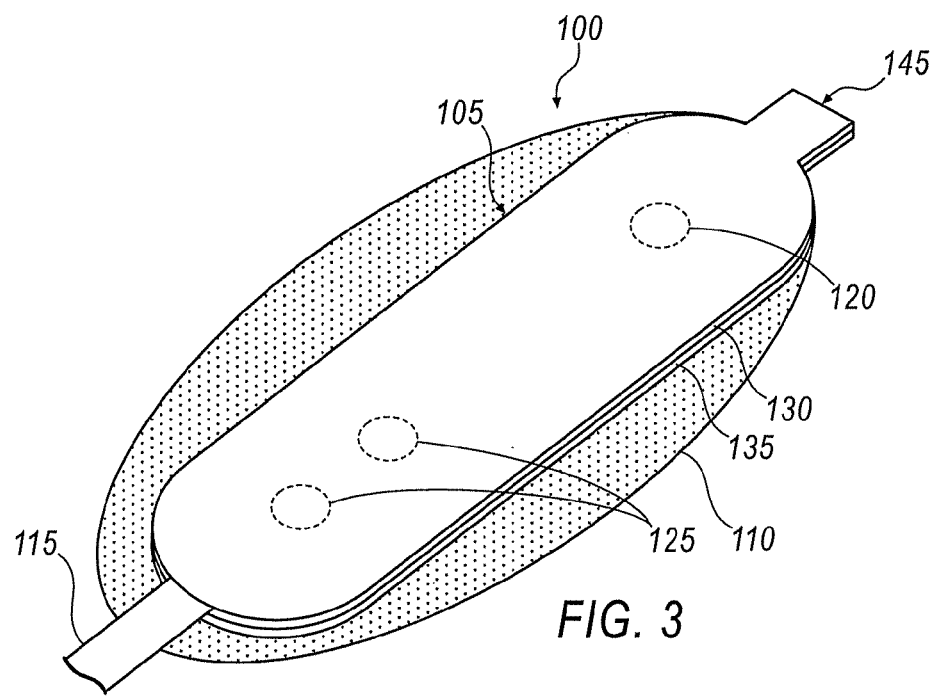
FIG. 3 illustrates the exemplary sensor FIG. 1 with the sensor pad defining a tab that extends beyond an edge of the adhesive layer.
Figure 4:
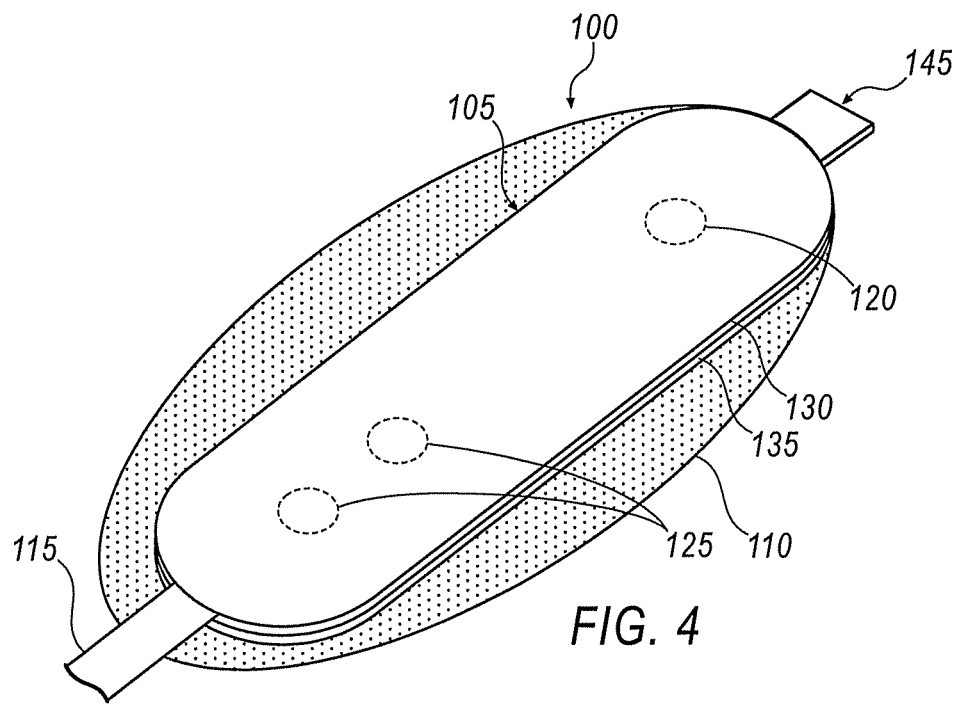
FIG. 4 illustrates the exemplary sensor of FIG. 1 where the tab is defined by a bottom layer of the sensor pad.

FIG. 3 illustrates another exemplary sensor 100 where the sensor pad 105 defines a tab 145 that extends beyond an edge of the adhesive layer 110. The clinician may remove the sensor 100 from the patient's body by pulling the tab 145, and thus the sensor pad 105, away from the patient's body. The tab 145 may be defined by the top layer 130, the bottom layer 135, or both. In the exemplary approach of FIG. 3, the tab 145 is defined by both the top layer 130 and the bottom layer 135. Alternatively, referring to FIG. 4, the tab 145 is defined by the bottom layer 135. In the exemplary approaches illustrated in FIGS. 3 and 4, the cable 115 is generally in line with the sensor pad 105 and the tab 145 extends beyond an edge of the adhesive layer 110, while at the opposite end of the sensor 100 (e.g., the side of the sensor 100 near the cable 115), the adhesive layer 110 extends beyond the perimeter of the sensor 100 as defined by the top layer 130 and the bottom layer 135.

Figure 5:
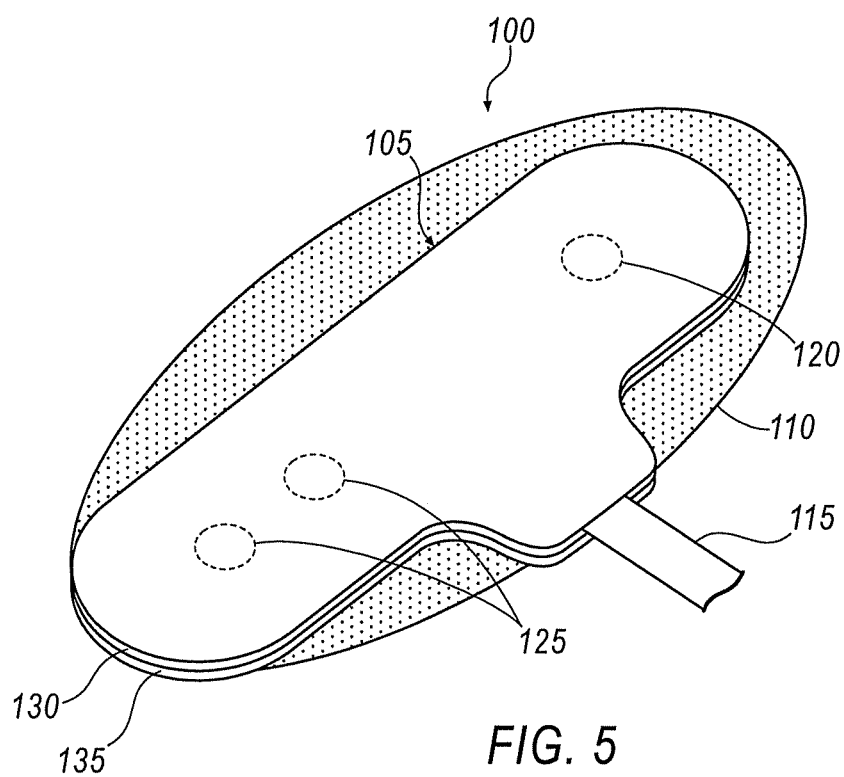
FIG. 5 illustrates another exemplary sensor having the adhesive layer offset from the sensor pad.

FIG. 5 illustrates another exemplary sensor 100 where the adhesive layer no is offset relative to the sensor pad 105 at a location spaced from the cable 115, for instance, to make removing the sensor 100 from the patient's body easier. The sensor 100 of FIG. 5 has a generally T-shaped configuration, i.e., the cable 115 extends in a direction that is generally orthogonal to the direction in which the sensor pad 105 extends. Part of the adhesive layer 110 extends beyond the perimeter defined by the sensor pad 105 and another part of the adhesive layer no is flush with the perimeter of the sensor pad 105. The top layer 130, the bottom layer 135, or both, may define the perimeter of the sensor pad 105. As illustrated, both the top layer 130 and the bottom layer 135 define the perimeter of the sensor pad 105.

Figure 6:
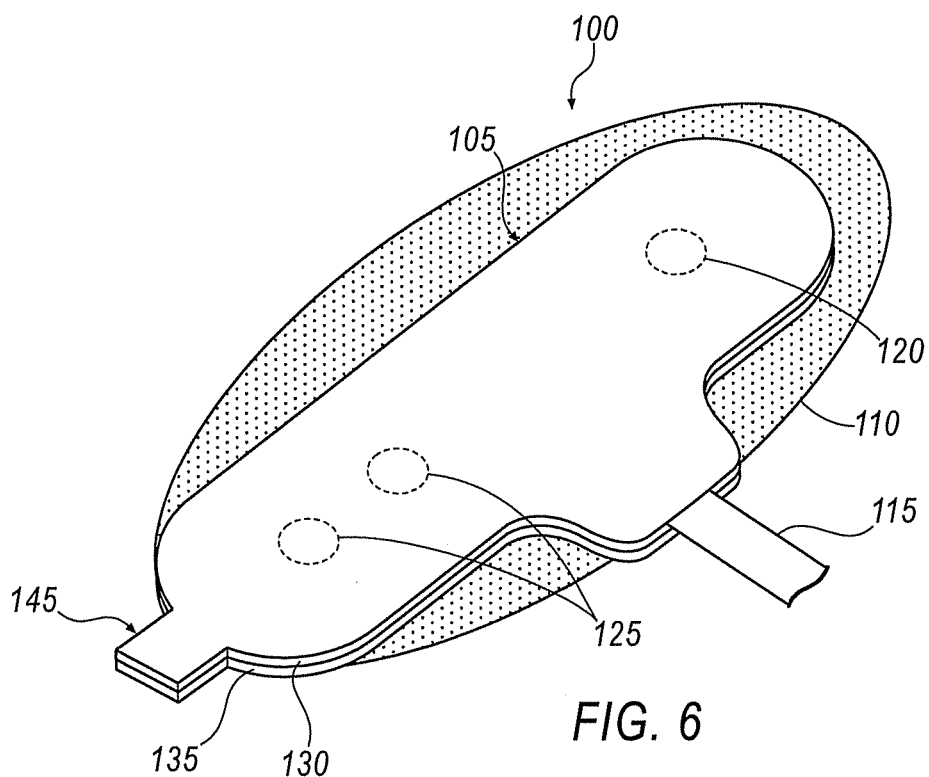
FIG. 6 illustrates the exemplary sensor FIG. 4 with the sensor pad defining a tab that extends beyond an edge of the adhesive layer.
Figure 7:
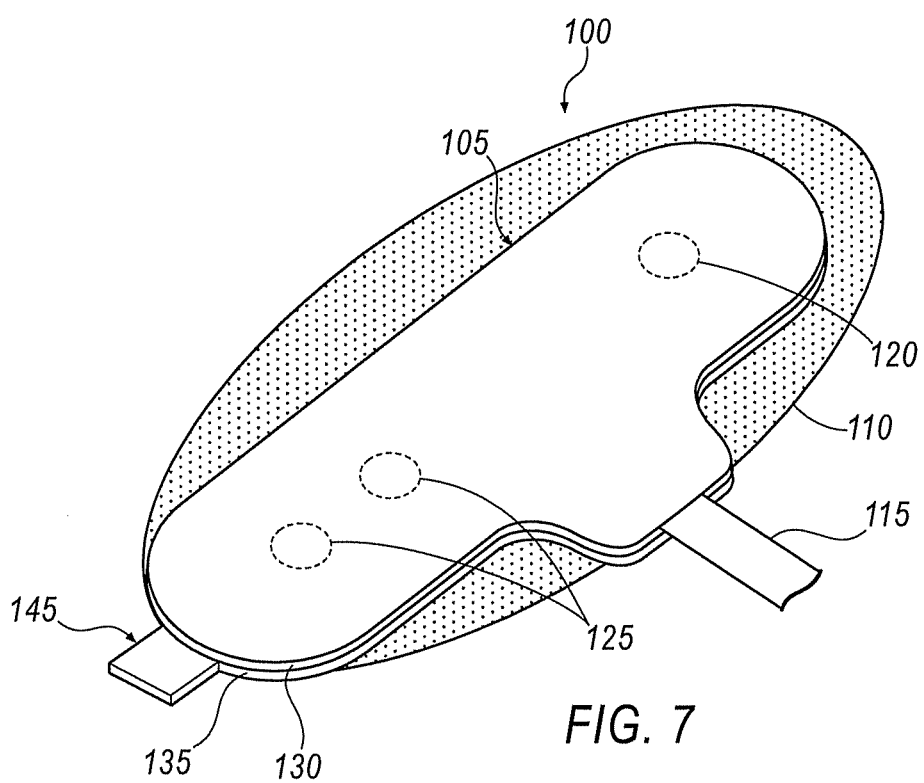
FIG. 7 illustrates the exemplary sensor of FIG. 4 where the tab is defined by a bottom layer of the sensor pad.

FIG. 6 illustrates an exemplary sensor 100 where the tab 145 is defined by the top layer 130 and the bottom layer 135. The tab 145 of the sensor 100 may alternatively be defined by just the top layer 130 or just the bottom layer 135. For example, with reference to FIG. 7, the tab 145 is defined by the bottom layer 135 and not the top layer 130. In the exemplary implementations of FIGS. 6 and 7, the tab 145 extends beyond an edge of the adhesive layer 110. However, at an opposite end of the sensor 100, the adhesive layer 110 extends beyond the perimeter defined by the sensor pad 105.

The sensors illustrated herein, including the various layers shown and described, are merely exemplary and not necessarily to scale. Indeed, the cross-sectional views are provided for illustrative purposes and ease of understanding and are not suggestive of the actual size of the layers used in the sensor. Indeed, the sensor and components that make up the sensor may have many different sizes and shapes.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claimed invention.

Accordingly, it is to be understood that the above description is intended to be illustrative and not restrictive. Many embodiments and applications other than the examples provided would be apparent upon reading the above description. The scope of the invention should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the invention is capable of modification and variation.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary.

The invention claimed is:

1. A sensor comprising:
   a sensor pad defining a perimeter and having a patient surface configured to be applied adjacent to a patient's skin, said patient surface being substantially free of adhesive;
   a light source disposed on the sensor pad and configured to generate near-infrared light and transmit the near-infrared light through part of a patient's body;
   a light detector disposed on the sensor pad and configured to receive near-infrared light generated by the light source after it has traveled through part of the patient's body, wherein the light received by the light detector indicates an amount of oxygen in the part of the patient's body through which the near-infrared light traveled;
   a cable extending from the perimeter of the sensor pad; and
   an adhesive layer disposed on the sensor pad, wherein one part of the adhesive layer extends beyond the perimeter of the sensor pad and another part of the adhesive layer at a location spaced from the cable does not extend beyond the perimeter of the sensor pad.

2. A sensor as set forth in claim 1, wherein part of the adhesive layer extends beyond the perimeter of the sensor pad and part of the sensor pad extends beyond an edge of the adhesive layer.

3. A sensor as set forth in claim 1, wherein the sensor pad includes a flexible material.

4. A sensor as set forth in claim 1, wherein the adhesive layer includes a flexible material.

5. A sensor as set forth in claim 1, wherein the adhesive layer includes a pressure sensitive adhesive.

6. A sensor as set forth in claim 1, wherein the adhesive layer includes a hydrocolloid adhesive.

7. A sensor as set forth in claim 1, wherein the light source includes at least one of a light emitting diode and a laser diode.

8. A sensor as set forth in claim 1, wherein the light detector includes a photodiode.

9. A sensor as set forth in claim 1, further comprising a liner disposed on the adhesive layer.

10. A sensor as set forth in claim 1, wherein the sensor pad includes a top layer and a bottom layer, and wherein the light source and the light detector are disposed between the top and bottom layers.

11. A sensor as set forth in claim 10, wherein the top and bottom layers each include a flexible material.

12. A sensor as set forth in claim 10, wherein the adhesive layer is disposed on the bottom layer of the sensor pad and wherein the adhesive layer is offset relative to the bottom layer.

13. A sensor as set forth in claim 12, wherein the perimeter of the sensor pad is at least partially defined by the bottom layer and wherein one part of the adhesive layer extends beyond the perimeter defined by the bottom layer and wherein another part of the adhesive layer is substantially flush with the perimeter defined by the bottom layer.

14. A sensor as set forth in claim 12, wherein part of the adhesive layer extends beyond the perimeter defined by the bottom layer and part bottom layer extends beyond an edge of the adhesive layer.

15. A sensor as set forth in claim 10, wherein the top layer includes a light blocking material.

16. A sensor as set forth in claim 1, wherein said part of said adhesive layer that does not extend beyond said sensor pad is substantially flush with the sensor pad.

17. A sensor as set forth in claim 1, further including a tab formed integrally with said sensor pad that extends beyond an edge of said adhesive layer.

18. A sensor comprising:
   a sensor pad having a top layer having a light blocking material and a bottom layer at least partially defining a perimeter of the sensor pad, said bottom layer having a patient surface configured to be applied adjacent to a patient's skin, said patient surface being substantially free of adhesive;
   a cable extending from the sensor pad;
   a light source disposed on the sensor pad between the top layer and the bottom layer and configured to generate near-infrared light and transmit the near-infrared light through part of a patient's body;
   a light detector disposed on the sensor pad between the top layer and the bottom layer and configured to receive near-infrared light generated by the light source after it has traveled through part of the patient's body, wherein the light received by the light detector indicates an amount of oxygen in the part of the patient's body through which the near-infrared light traveled; and
   an adhesive layer disposed on the top layer and spaced from the bottom layer, wherein the adhesive layer is offset relative to the bottom layer of the sensor pad such that one part of the adhesive layer extends beyond the perimeter defined by the bottom layer and wherein another part of the adhesive layer at a location spaced from the cable does not extend beyond the perimeter of the sensor pad.

19. A sensor as set forth in claim 18, wherein part of the adhesive layer extends beyond the perimeter defined by the bottom layer and part bottom layer extends beyond an edge of the adhesive layer.

20. A sensor as set forth in claim 18, wherein the top layer, the bottom layer, and the adhesive layer each include a flexible material.

21. A sensor as set forth in claim 18, wherein said part of said adhesive layer that does not extend beyond said sensor pad is substantially flush with the sensor pad.

* * * * *